United States Patent [19]
Arashima et al.

[11] Patent Number: 6,030,376
[45] Date of Patent: Feb. 29, 2000

[54] CORNEAL SURGICAL APPARATUS

[75] Inventors: Mikio Arashima, Gamagori; Toshifumi Sumiya, Nukata-gun; Hirohiko Hanai, Gamagori, all of Japan

[73] Assignee: Nidek Co., Ltd., Japan

[21] Appl. No.: 08/998,081

[22] Filed: Dec. 24, 1997

[30] Foreign Application Priority Data

Dec. 27, 1996 [JP] Japan .................................. 8-359007

[51] Int. Cl.⁷ ............................. A61B 17/36; A61B 3/12; A61N 5/02
[52] U.S. Cl. ................................................ 606/4; 606/12
[58] Field of Search ................................. 606/4, 5, 6, 10, 606/11, 12

[56] References Cited

U.S. PATENT DOCUMENTS

| | | | |
|---|---|---|---|
| 4,579,430 | 4/1986 | Bille | 606/4 |
| 4,891,043 | 1/1990 | Zeimer et al. | 604/20 |
| 5,395,356 | 3/1995 | King et al. | 606/4 |
| 5,507,799 | 4/1996 | Sumiya | 606/5 |
| 5,556,395 | 9/1996 | Shimmick et al. | 606/4 |
| 5,562,656 | 10/1996 | Sumiya | 606/4 |
| 5,620,436 | 4/1997 | Lang et al. | 606/4 |
| 5,637,109 | 6/1997 | Sumiya | 606/5 |
| 5,643,249 | 7/1997 | Amano | 606/4 |
| 5,865,829 | 2/1999 | Kitajima | 606/3 |

*Primary Examiner*—Linda C. M. Dvorak
*Assistant Examiner*—Sonya Harris-Ogugua
*Attorney, Agent, or Firm*—Finnegan, Henderson, Farabow, Garrett & Dunner, L.L.P.

[57] ABSTRACT

An ophthalmic operating apparatus comprising an observation optical system for observing an anterior part of patient's eye, a laser beam irradiating optical system for irradiating a laser beam for treatment on the patient's eye, a moving device for moving the laser beam irradiating optical system relatively with respect to the patient's eye, an illumination optical system for projecting an illumination light from a pupil of the patient's eye so that the anterior part being illuminated by a reflected light at a fundus of the patient's eye from a rear side, and a photographic element for photographing a retro-illumination image of the anterior part illuminated by the illumination optical system.

18 Claims, 10 Drawing Sheets

PUPIL PART

CORNEAL SURGICAL APPARATUS

BACKGROUND OF THE INVENTION

1. Field of the Invention

The present invention relates to an ophthalmic operating apparatus for performing treatment by irradiating a laser beam for treatment onto a patient's eye, and more particularly to the apparatus providing an alignment mechanism for delivering the laser beam for treatment to a desired position for the patient's eye, or for delivering the laser beam to the desired position by tracking a movement of the patient's eye, and an observing mechanism for observing unevenness of a cornea of the patient's eye just after the completion of the treatment.

2. Description of Related Art

An ophthalmic operating apparatus for operating upon a cornea with using an excimer laser beam is well known as an ophthalmic operating apparatus for performing treatment by irradiating the laser beam for treatment on the patient's eye. The apparatus is used for removing a diseased portion on a corneal surface by irradiating the excimer laser beam on the corneal surface or for correcting ametropia by ablating the corneal surface so as to change corneal curvature. By using this apparatus, the patient's eye is fixed with a fixation target, so that an operator starts alignment to make the patient's eye and an irradiation optical system be under the desired condition with observing an alignment target. After the alignment is completed, the ablation is performed within a desired range only for a set level by controlling the apparatus.

Also, after the corneal surface is ablated with using this type of the ophthalmic operating apparatus, the corneal shape is to be observed in order to-confirm that the cornea of the patient's eye is ablated appropriately. This observation was the criterion for estimating corneal apacification, for confirming a fixating deviation of the patient's eye, and for determining whether another operation is required once more.

Further, upon LASIK operation, flap (corneal epithelium and a partial of stroma) is peeled partially, then the excimer laser beam is irradiated. Then, the flap is returned back, where it was, so as to be sticked thereon. At the time of being returned, the sticked condition is observed, especially whether air is contained or not between the flap is observed.

However, although the fixation target is fixed on the patient's eye, some patients of which eyes are defective fixation have a problem that their eyes are not stable. Therefore, once it is confirmed that the eye is moved during the alignment or laser beam irradiation, the laser beam irradiation should be stopped and the alignment should be begun from the first step. As a result, doing the alignment repeatedly will impose such a burden that the operation time may be prolonged on both the patient and the operator. Also, the patient of which eye is moved frequently has much burden.

Besides, if the laser beam irradiation is continued without any notice of movement of the patient's eye, the surface of the cornea will not be ablated to be an expected shape. Consequently, the postoperative refractive power would be effected.

Further, it may be intricate that the postoperative condition is estimated with using another apparatus, and it may be another burden with the patient and the operator.

SUMMARY OF THE INVENTION

The present invention has been made in view of the above circumstances and has an object to overcome the above problems, and to provide an ophthalmic operating apparatus which may make it easy to align the laser beam irradiating optical system with the patient's eye, and may allow the treatment to be appropriate.

Also, another object of the present invention provides the apparatus being capable of lightening burdens, which effect on both the patient and the operator, by reducing such trouble that the patient and the operator have to move among plural apparatuses and by shortening the operation time.

Additional objects and advantages of the invention will be set forth in part in the description which follows and in part will be obvious from the description, or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, an ophthalmic operating apparatus comprises an observation optical system for observing an anterior part of a patient's eye, a laser beam irradiating optical system for irradiating a laser beam for treatment on the patient's eye, moving means for moving the laser beam irradiating optical system relatively with respect to the patient's eye, an illumination optical system for protecting an illumination light from a pupil of the patient's eye so that the anterior part of the patient's eye may be illuminated from a rear side by a light reflected at a fundus of the patient's eye, and a photographic element for photographing a retro-illumination image of the anterior part of the patient's eye which is illuminated by the illumination optical system.

In another aspect of the present invention, an ophthalmic operating apparatus comprises a laser beam irradiating optical system for irradiating a laser beam for treatment on a patient's eye, moving means for moving the laser beam irradiating optical system to a direction of optical axis and a direction intersecting at right angles to the optical axis, an observation optical system for observing an anterior part of the patient's eye by irradiating a visible light on the patient's eye, a retro-illumination image detecting optical system for illuminating a near-infrared light beam on the patient's eye so that the anterior part of the patient's eye may be illuminated from a rear side by a reflected light at a fundus of the patient's eye and then for detecting the reflected light, image processing means for obtaining a position of a pupil center based on a retro-illumination image of the anterior part of the patient's eye which is detected by the retro-illumination image detecting optical system, and controlling means for driving and controlling the moving means based on the signal of the position of the pupil center which is obtained by the image processing means so that an optical axis of the laser beam irradiating optical system and the position of the pupil center may be congruent.

As described above, and in accordance with the present invention, the apparatus enables to track the movement of the patient's eye even though the eye is moved during the alignment or the laser beam irradiation operation, so that the shift of the irradiated area can be prevented in order to achieve the appropriate treatment.

Also, in accordance with the present invention, since a reflected light flux from the fundus of the eye is used for detecting the pupil position, the pupil position may be detected definitely without being effected by any change of the corneal shape which is caused by the ablation. Therefore, the tracking of the eyeball can be achieved accurately.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention.

In the drawings.

DETAILED DESCRIPTION OF THE PREFERRED EMBODIMENTS

A detailed description of the present invention is provided below with reference to the accompanying drawings.

Whole Structure

Figure 1:
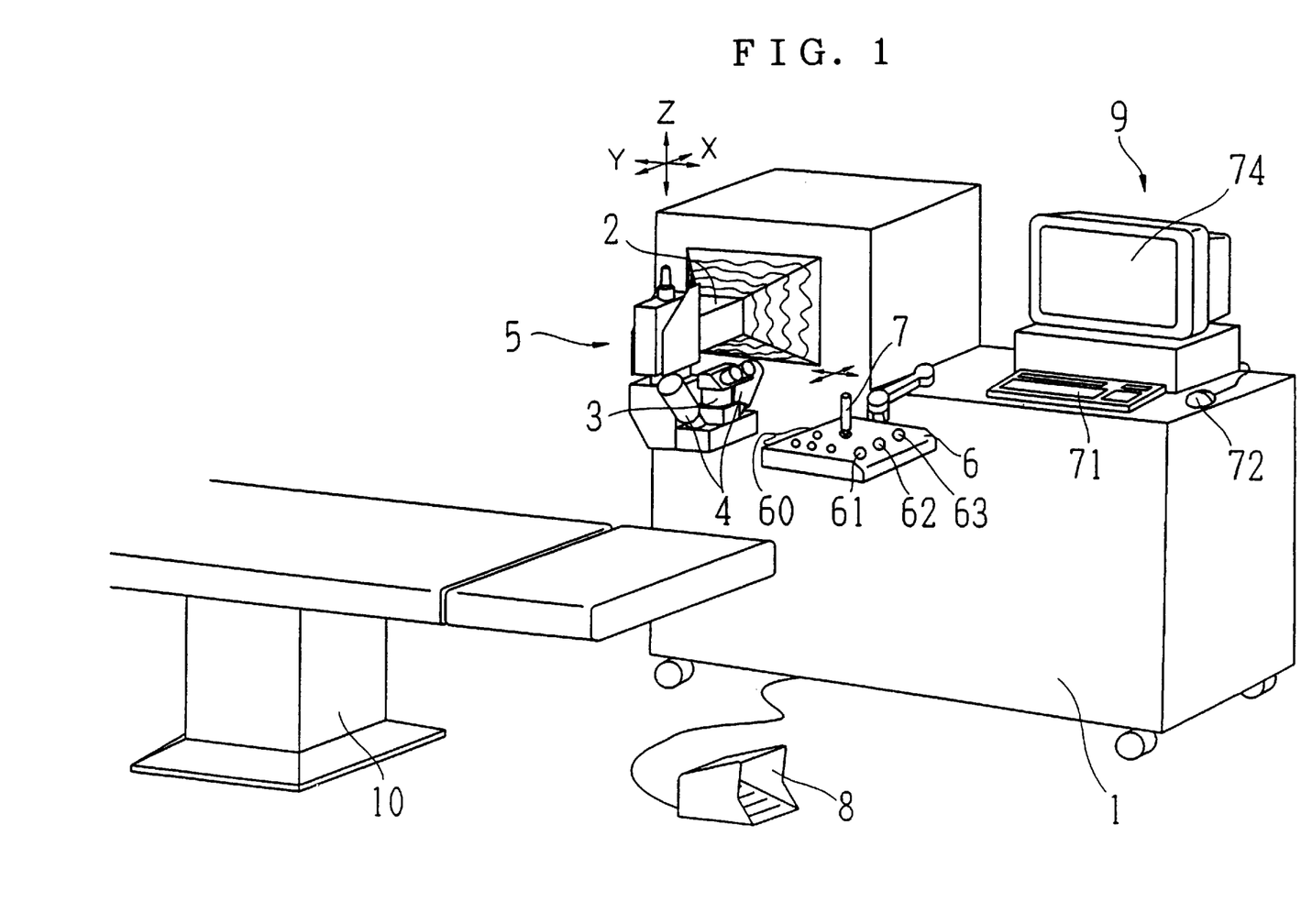
FIG. 1 is a view showing a whole structure of an ophthalmic apparatus for operating upon a cornea of the preferred embodiment of the present invention.
Figure 2:
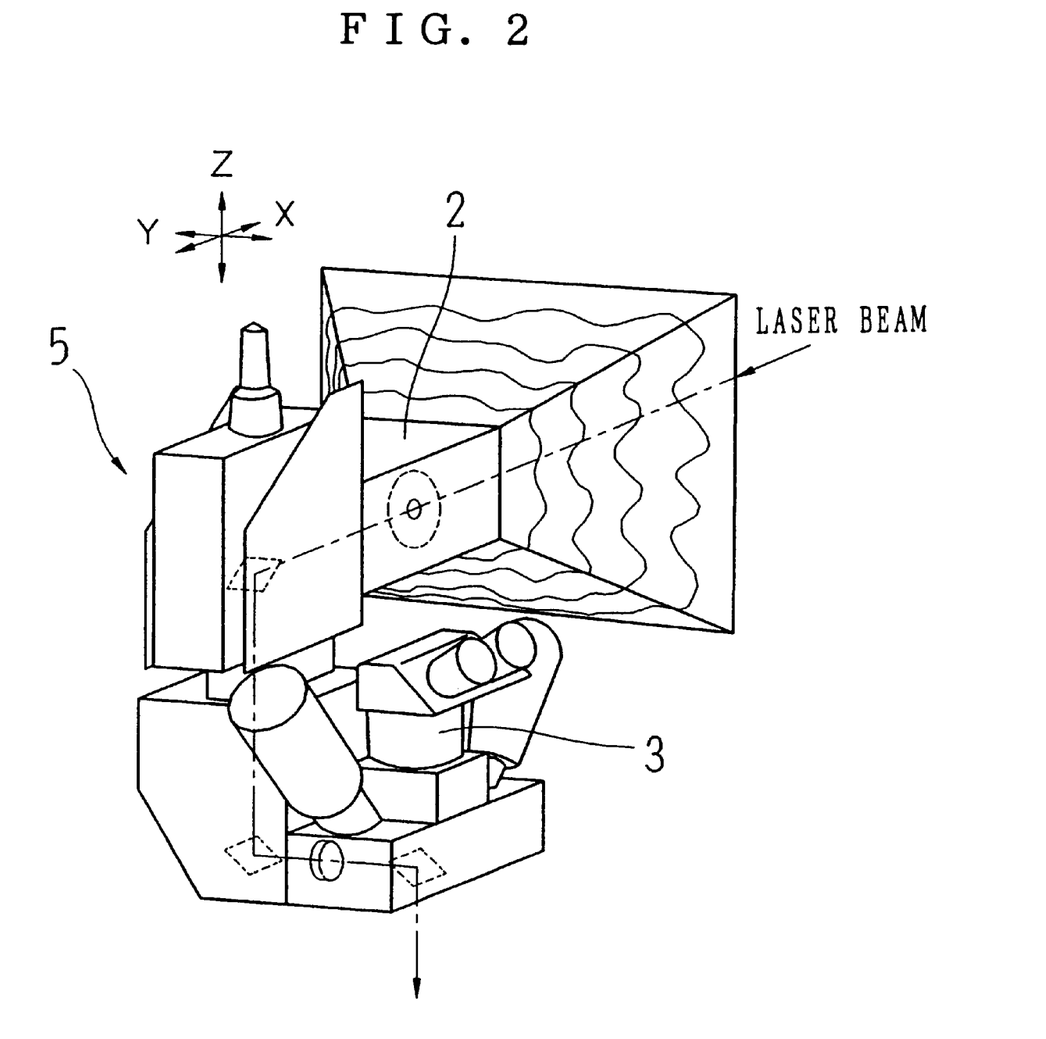
FIG. 2 is a view showing an arrangement of optical elements inside an arm part of the ophthalmic apparatus for operating upon a cornea of the preferred embodiment.
Figure 3:
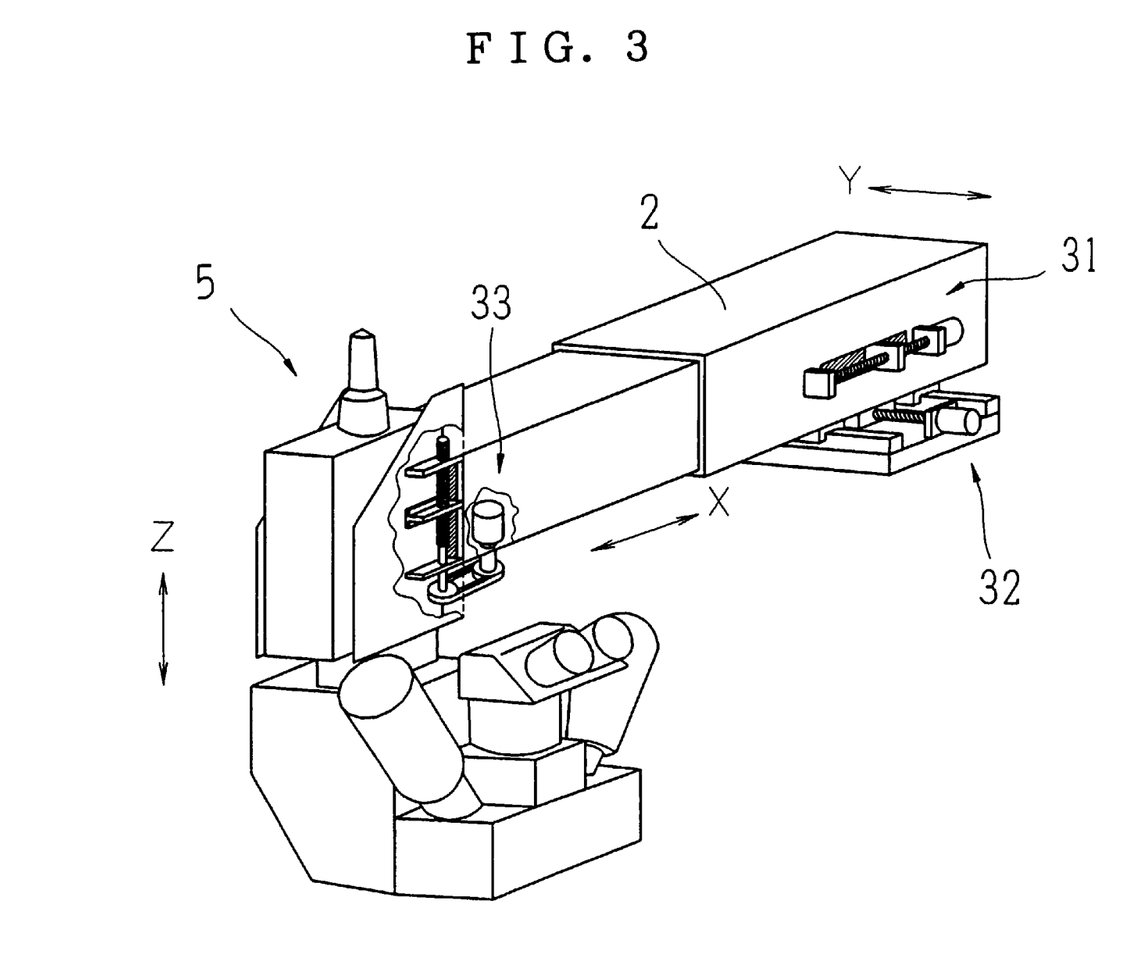
FIG. 3 is a view showing a moving mechanism of the arm part of the ophthalmic apparatus for operating upon a cornea of the preferred embodiment.

FIG. 1 is a whole structure of an apparatus for operating upon a cornea with using an excimer laser beam. An excimer laser beam source and the like are built-in a body 1 of the apparatus The laser beam from the excimer laser beam source is reflected at a mirror inside the body 1 so as to be delivered to an arm part 2. The arm part 2 is composed of a binocular microscope 3 for observing a patient's eye, an illumination part 4, a laser beam irradiation outlet which is not illustrated herein, and an observation optical part 5 having an optical system for detecting eye-position, and the like, which will be described hereinafter. The laser beam is delivered to the patient's eye by optical elements such as a mirror, or the like, which are arranged inside the arm part 2 and the observation optical part 5 (see FIG. 2). The arm part 2 is moved in X-direction (a lateral direction against an operator) by a X-direction arm driving device 31, and moved in Y-direction (a toward-away from the operator) by a Y-direction arm driving device 32. Also, the observation optical part 5 is moved in Z-direction by a Z-direction driving device 33. The driving devices 31, 32, and 33 are composed of motors, sliding mechanisms and the like.

A controller 6 provides a joystick 7 for supplying signal to drive the arm part 2 in X-Y directions, a focus set switch 60 for starting the alignment in Z-direction, an automatic alignment switch 61 for setting a switching of ON/OFF for the automatic alignment, Ready switch 62 for switching from the condition on standby to the possible condition of the laser beam irradiation, V. facter observing changing-over switch 63 for observing a unevenness of a postoperative cornea (hereinafter, it is called V. facter), and the like. A setting menu screen for setting operating condition and a retro-illumination image of anterior part of the patient's eye at the time of examining V. facter is displayed on a monitor 74. Numeral 8 is a foot switch for forwarding a laser-emitting signal, and in a computer 9, various data necessary for operating condition are inputted, and the data of the laser beam irradiation are calculated, displayed and memorized. Also the computer 9 reads an observed image of V. facter so as to display, analyze and memorize. Numeral 10 is a bed for letting the patient lie down on.

Structure of each System

Optical Systems

Figure 4:
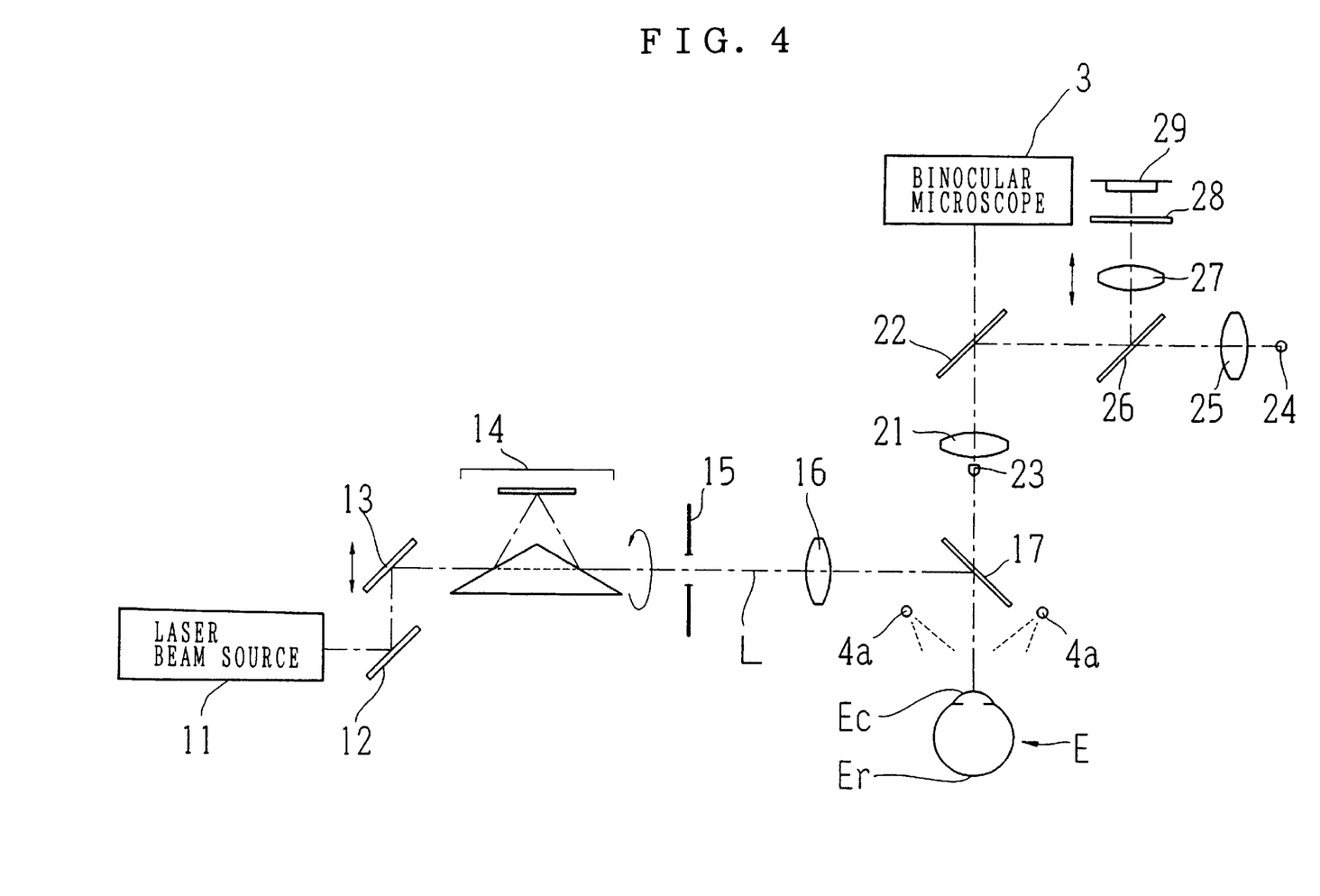
FIG. 4 is a view showing an outline diagram of optical system of the ophthalmic apparatus for operating upon a cornea of the preferred embodiment.

FIG. 4 is a view showing an outline diagram of optical systems of the preferred embodiment.

(a) Laser irradiation optical system

A laser beam source 11 emits the excimer laser beam having wavelength of 193 nm. A plane mirror 12 reflects the laser beam, which is emitted in a horizontal direction from the laser beam source 11, upward 90'. A plane mirror 13 is movable in a vertical direction (in an arrow direction) in order to deflect the laser beam to the horizontal direction once more. An image rotator 14 rotates the laser beam around an optical axis L. An aperture 15 restricts an irradiation area of the laser beam, and its aperture diameters may be changed by an aperture driving device which is not illustrated herein. A projective lens 16 projects the aperture 15 on a cornea Ec of a patient's eye E. The aperture 15 is at a conjugate position with the cornea Ec with respect to the projective lens 16, and the area restricted by the aperture 15 is projected on the cornea, thereby the area to be ablated is restricted.

The laser beam having a rectangular section which is emitted from the laser beam source 11 is moved in a constant direction by a parallel movement of the mirror 13 so as to cover the whole of aperture area of the aperture 15. The ablation by the moving control of the mirror 13 and the aperture control of the aperture 15 is described in Japanese Patent Publication Laid-Open No. 4-242644 by the applicant of the present invention for reference (corresponding to the U.S. Pat. No. 5,507,799).

A dichroic mirror 17 has a characteristic of reflecting the excimer laser beam and transmitting a visible ray and an infrared ray, and causes the optical axis of the laser irradiation optical system to be coaxial with the optical axis of the objective lens of a below-mentioned observation optical system.

(b) Observation optical system

Numeral 21 is an objective lens, and a dichroic mirror 22 has a characteristic of transmitting the visible ray and of reflecting the infrared ray. The image of the anterior part of the eye E which is illuminated by a visible illuminating light source 4a inside the illumination part 4 is incident on the binocular microscope part 3 via the dichroic mirror 17, objective lens 21 and dichroic mirror 22. The operator observes the eye E from the binocular microscope part 3. A reticle plate which is not shown is inserted into the observation optical system, therefore the reticle plate may be a standard point for the alignment of X-Y directions of the eye E.

Also, a target projecting optical system, which is composed of two pieces of slits for performing the alignment in the Z-direction, is arranged in the observation optical system (see Japanese Patent Publication Laid-Open No. 6-47001 corresponding to U.S. Pat. No. 5,562,656), filed by the present applicant.

A fixation light 23 is positioned on the optical axis of the objective lens 21.

(c)Retro-illumination image detecting optical system

Numeral 24 is an illumination light source such as LED or the like, for emitting light within a range of near-infrared ray, 25 is a collective lens, 26 is a beam splitter, 27 is a photographic lens, 28 is an infrared-light transmitting filter, and 29 is CCD camera having sensitivities within a range of near-infrared ray. The photographic lens 27 is movable in an arrow direction by a driving device which is not shown. By Movement of the photographic lens 27, during the operation, a photographing surface of CCD camera 29 is arranged optically to be approximately conjugate with the position close to the pupil of the eye E with respect to the photographic lens 27 and the objective lens 21. After the operation is completed, the photographing surface is arranged optically to be approximately conjugate with the position close to the cornea of the eye E in order to estimate the operation result.

After the infrared light emitted from the illumination light source 24 passes through the collective lens 25 and the beam splitter 26, then is reflected at the dichroic mirror 22 so as to be coaxial with a center axis of a binocular observation system. The light which is reflected at the dichroic mirror 22 is changed to be a parallel light by the objective lens 21, then is transmitted to the eye E. The light from the pupil of the eye E is reflected at a fundus Er, so that the anterior part may be illuminated from the rear side via a crystalline lens. Then, the reflected light passes through the dichroic Juror 17, the objective lens 21, the dichroic mirror 22, the beam splitter 26, the photographic lens 27 and the infrared-light transmitting filter 28 so as to be imaged on the photographing surface of CCD camera 29. At this time, the infrared-light transmitting filter 28 blocks off the visible light which is reflected slightly at the dichroic mirror 22.

Signal Processing System

Figure 5:
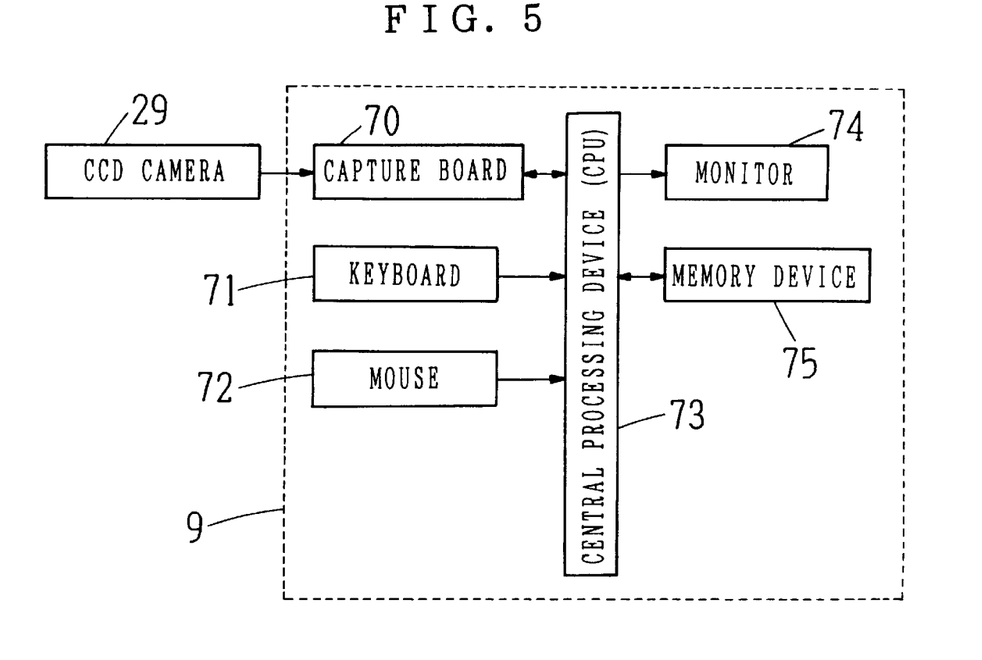
FIG. 5 is a view showing an outline of analyzing system of the ophthalmic apparatus for operating upon a cornea of the preferred embodiment.

Next, the details of processing and analysis of signal detected by the retro-illumination image detecting optical system will be described herein with using a block diagram showing an outline of analyzing system in FIG. 5.

Concerning the image photographed by CCD camera 29, the analog signal is converted to the digital signal by a capture board 70 inside the computer 9. Then, the image is displayed simultaneously on the monitor 74 passed through a central processing unit (CPU) 73. Upon detecting V. facter, when the operator inputs a signal by using a keyboard 71 or a mouse 72, the inputted signal is forwarded to the capture board 70 from the CPU 73. The capture board 70 which receives the signal cuts one frame from continuous images which are forwarded from CCD camera 29 so as to transmit it as a digital-image signal to the CPU 73. The transmitted digital-image signals are accumulated in a memory device 75 under the control of the CPU 73.

(a) Detection of eye position

Figure 6:
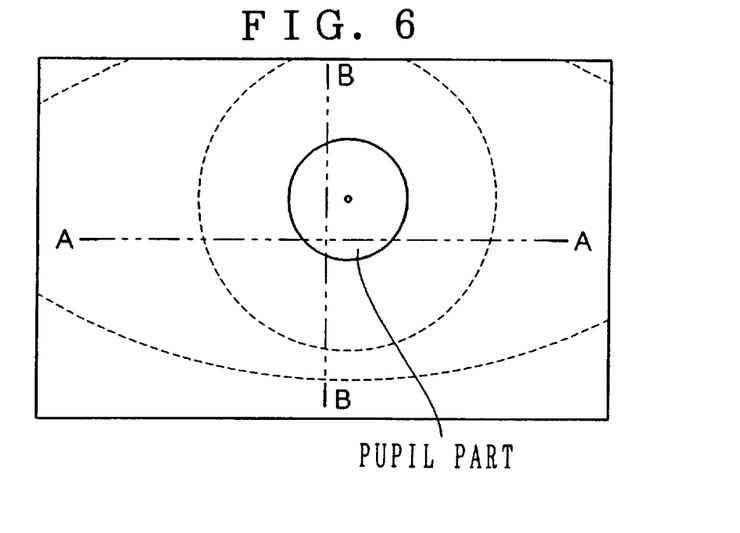
FIG. 6 is a view showing an image of a pupil part photographed by CCD camera of the ophthalmic apparatus for operating upon a cornea of the preferred embodiment.

The eye position is detected by the computer 9 as follows. FIG. 6 is a view showing an image of the pupil part which is photographed by CCD camera 29 (since the infrared ray of interior illumination light is not blocked, the infrared ray is slightly contained. Therefore, although the anterior part except the pupil part is photographed by CCD camera 29, there is a little quantity of light), FIG. 7(a) is a view showing distribution of a quantity of light on a line A—A which is obtained on the basis of the photographic signal from CCD camera 29, and FIG. 7(b) is a view showing distribution of differential value when the distribution of quantity of light is differentiated in FIG. 7(a).

Figure 7:
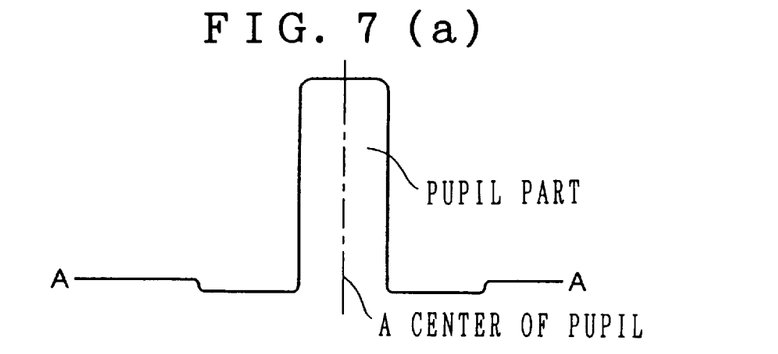
FIG. 7(a) is a view showing distribution of a quantity of light on a line A—A shown in FIG. 6.
FIG. 7(b) is a view showing distribution of differential value on a line A—A shown in FIG. 6.

As shown in FIG. 7(a), since the quantity of light of the image of the pupil part remarkably increases compared with other peripheral parts, a variation point may be obtained by differentiating its quantity of light. As shown in FIG. 7(b), since the differential value is outstanding at the remarkable part of distribution variation of the quantity of light, the maximum $D_{MAX}$ and the minimum $D_{MIN}$ may be detected as pupil edge of a lateral direction (A—A direction). Further, as a result of detecting the pupil edge, its center position, in other words, the center position of the pupil of the lateral direction may be obtained. In the same way, based on the differential data of the distribution of the quantity of light on a line B—B of a longitudinal direction, the center position of the pupil of the longitudinal direction may be obtained. As a result, by obtaining the center positions of the pupil of the both directions, the center position of the pupil with respect to the optical axis of the detecting optical system (optical axis of the laser irradiation optical system) that is adjusted to a predetermined positional relationship on the photographic element of CCD camera 29 may be obtained. It is preferable that the detecting lines of lateral and longitudinal directions find the distributed information of the quantity of light for plural lines with the center at the middle of the photographing element of CCD camera 29, and then the information thereof are to be averaged. Although corneal reflection luminous point caused by the light source 24 is detected on CCD camera 29, the effect may be removed by appropriately setting a threshold level for detecting the pupil edge corresponding to the quantity of light at the pupil part. The corneal reflection caused by the illumination light source 24 may be omitted by providing deflection plates, of which deflection axes intersect at right angles, for both the illumination light source 24 side and CCD camera 29 side which are separated by the beam splitter 26.

(b) Detection of V. facter

Figure 8:
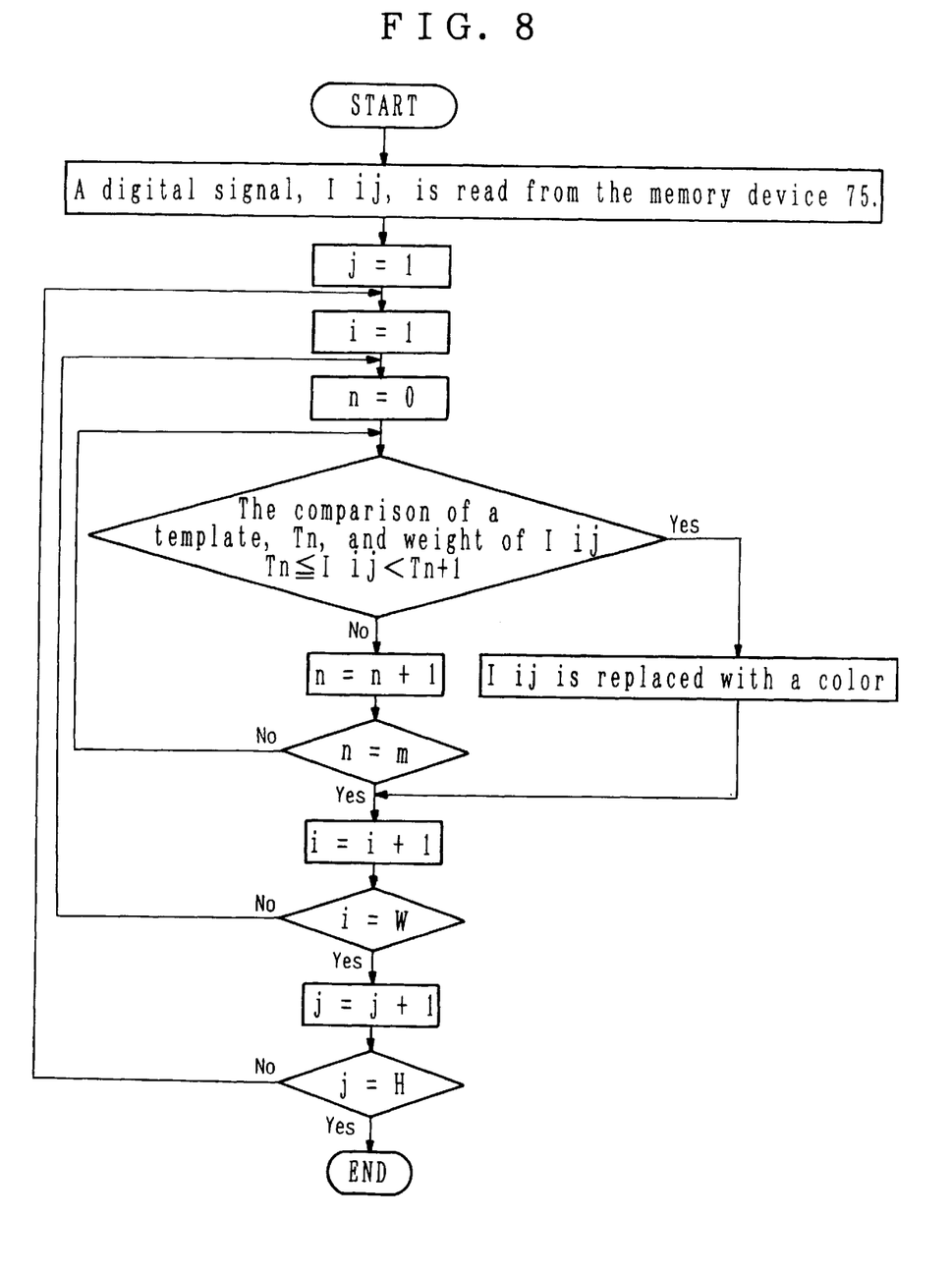
FIG. 8 is a flowchart for analyzing process of the ophthalmic apparatus for operating upon a cornea of the preferred embodiment.

Next, the analysis processing will be described based on a flowchart showing the analysis processing of the preferred embodiment shown in FIG. 8 and a diagram of digital image accumulated in the apparatus of the preferred embodiment shown in FIG. 9.

Figure 9:
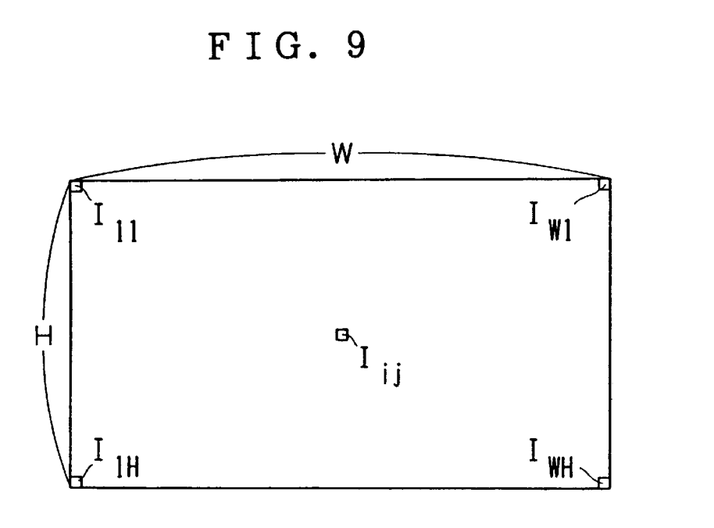
FIG. 9 is a view for explaining a digital image which is accumulated in the ophthalmic apparatus for operating upon a cornea of the preferred embodiment.

The accumulated image is digital-processed, and FIG. 9 shows an arrangement. The image is indicated as $I_{1J}$. The image is read by the CPU 73 from the memory device 75, so that every one pixel of the image may be detected in order. The detected direction is performed from the left-upper point $I_{11}$ toward the lateral direction in order so as to be detected until the right-upper part $I_{W1}$. Then, it is started once more from the left-lower point $I_{21}$, to be detected to the lateral direction. This process is repeated until the right-lower point $I_{WH}$. Then a weight of one pixel which is detected is compared with a defined template each other, if the weight of detected one pixel is contained within the defined template, the detected one pixel is replaced by a color of the defined template. The definition of template is shown as following expression.

$T_n \leq$ color n$<T_{n-1}$ (n=0~m)

The one pixel which is replaced by a color is indicated in the same order at the time of detecting. The same processing is performed at the whole range of image, then an image of a color map may be displayed. Also, the ablation area may be displayed as a numerical value or graph to what degree is occupied by each color.

Figure 10:
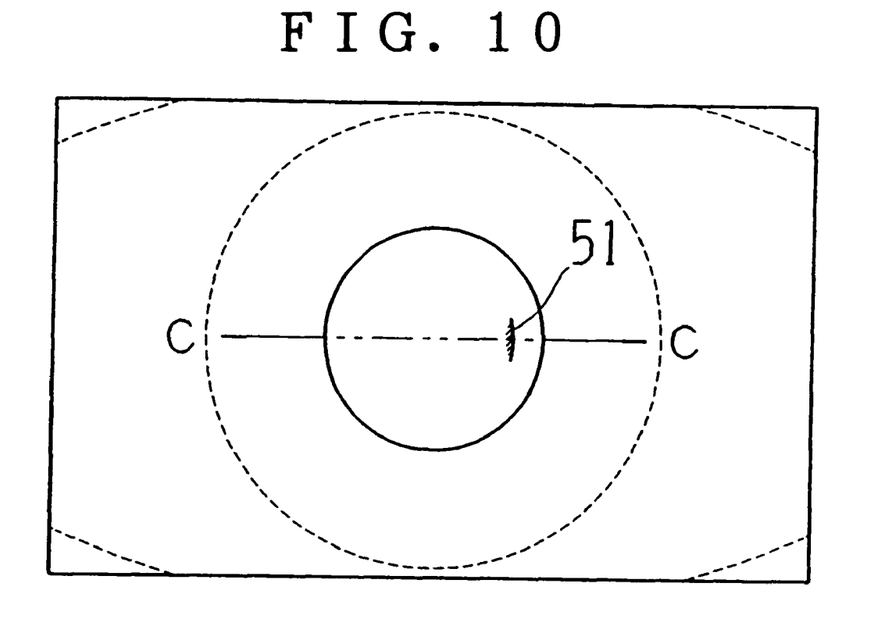
FIG. 10 is a view showing a sample of a postoperative retro-illumination image of an anterior part of an patient's eye which is displayed on a monitor of the ophthalmic apparatus for operating upon a cornea of the preferred embodiment.
Figure 11:
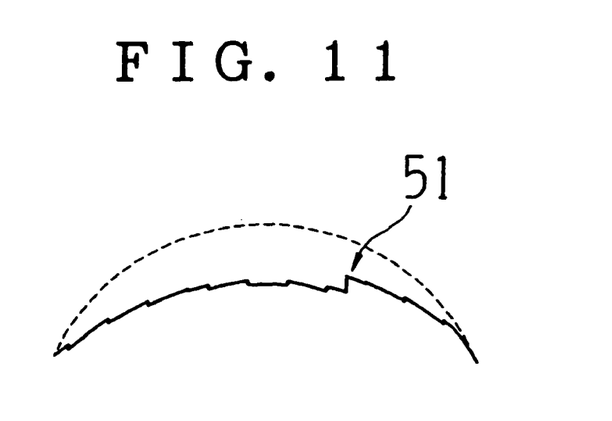
FIG. 11 is a view showing a sectional shape of a cornea of the patient's eye which is equivalent to a sectional part C—C in FIG. 10.

FIG. 10 is a sample of a postoperative retro-illumination image of the anterior part of the patient's eye which is displayed on the monitor 74. FIG. 11 is a sectional shape of the cornea of the patient's eye which is equivalent to a sectional part C—C (see FIG. 10) As described above, since the cornea is ablated with the laser beam irradiation by gradually enlarging the aperture 15, the sectional shape of the cornea becomes a stair-shape in a micro view. In case that the cornea is uniformly ablated to be a desired shape, the pupil part of the anterior part of the patient's eye which is displayed on the monitor 74 may be observed as an uniformed bright-colored image.

On the other hand, since the patient's eye is moved during the operation, the cornea may fail to be ablated to be a desired shape. Therefore, parts of ablation edge which should be a stair-shape may overlap each other, then it results in that edge parts having an improper height may be formed. Numeral 51 shown in FIG. 10 is a shadow which is formed upon the improper ablation. In the shadow 51, some of reflection light from the fundus are not transmitted to CCD camera 29 because of refraction or the like. Therefore, the quantity of light which is detected by CCD camera 29 is decreased, as a result, it appears as a dark shadow on the monitor 74.

Based on the shadow 51 displayed on the monitor 74, the operator judges whether the another operation should be performed once more or not. However, in the case that it is impossible to judge based on only the shadow 51 which is displayed on the monitor 74, the image analysis will be performed to judge appropriately.

Figure 12:
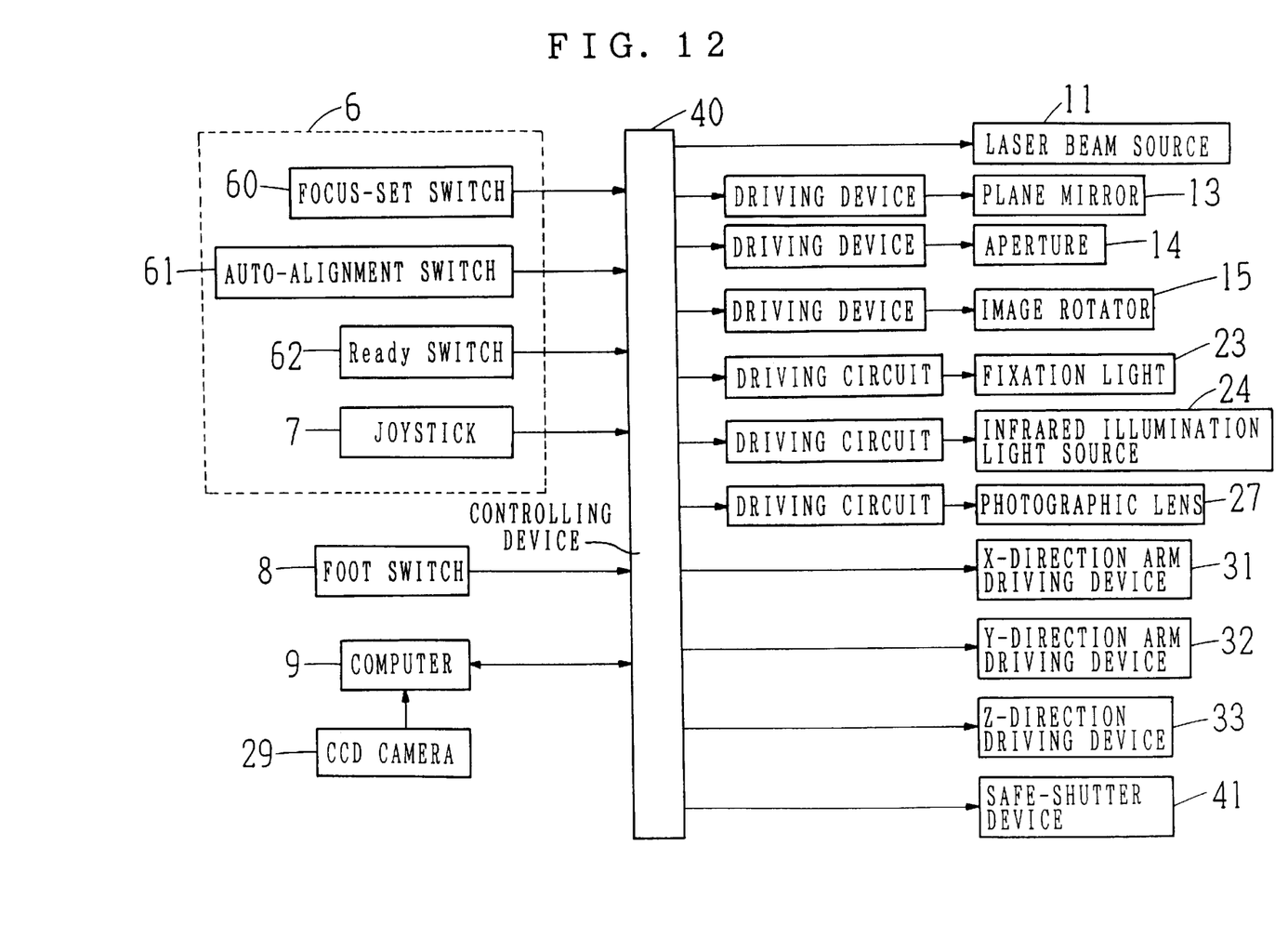
FIG. 12 is a block diagram of control system of the ophthalmic apparatus for operating upon a cornea of the preferred embodiment.

Concerning the apparatus having the above-mentioned structure, the operation method will be explained based on a block diagram of detailed control system shown in FIG. 12.

By turning on the power source of the apparatus to start the system, a menu screen is displayed on the monitor 74 of the computer 9. There are two kinds of operation modes of operating upon a cornea by using the excimer laser beam, one is a refractive correcting operation (PRK: photorefractive keratectomy) and another is a cure operation for ablating a corneal surface (PTK: phototherapeutic keratectomy). In this stage, the PRK method is to be selected from the menu screen. The operator inputs each various data of refractive power of the patient's eye E and operation condition, which are examined beforehand, with the keyboard 71 of the computer 9. The computer 9 calculates the ablating amount of the cornea based on the inputted data. The calculated operation data is transmitted to the controlling device 40 by operating the keyboard 71.

When the input preparation is completed, the operator lets the patient lie down on the bed 10, so that the observation optical part 5 providing a laser irradiating outlet is set above the eye E. Each light source is turned on, and the fixation light 23 is fixed to the eye E.

The operator observes the anterior part of the eye E illuminated by the illumination part 4 though the binocular microscope 3. By handling the joystick 7, the alignment of X-Y directions may be performed so that the reticle (is not illustrated) and the pupil may be a predetermined positional relationship, and then the alignment of Z-direction may be performed by operating the focus-set switch 60.

The controlling device 40 operates each driving devices 31, 32, and 33 by signals of the joystick 7 and the focus-set switch 60 so as to move the arm part 2 in X-Y directions and to move the observation optical part 5 in Z-direction Upon the alignment performance, based on the detection of the pupil center by an eye position detecting system, the automatic alignment may be selected in order to start alignment by controlling the operations of the X-direction arm driving device 31 and the Y-direction arm driving device 32.

Figure 13:
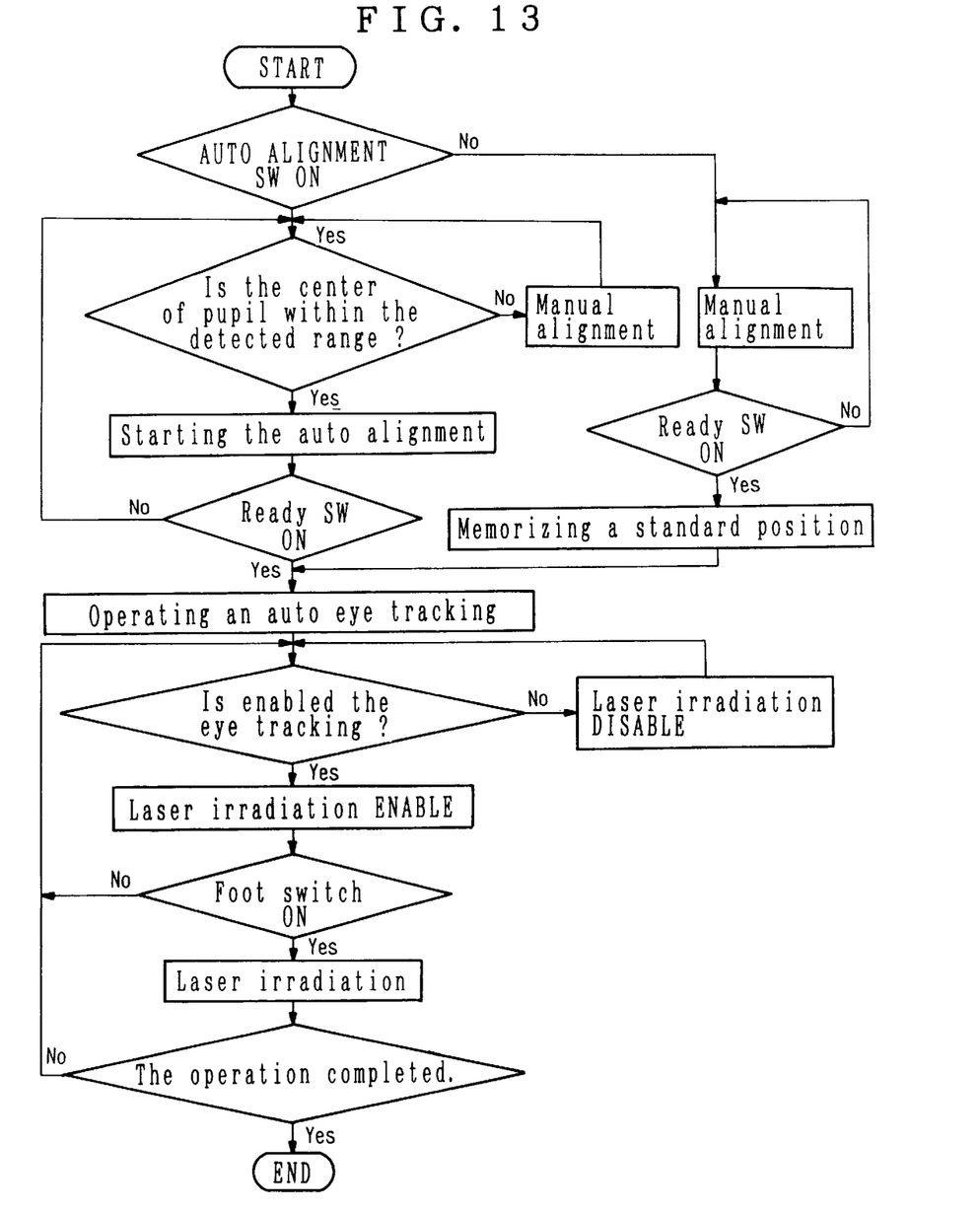
FIG. 13 is a flowchart for explaining performance of automatic alignment and tracking the patient's eye of the ophthalmic apparatus for operating upon a cornea of the preferred embodiment.

The automatic alignment is started by turning on the automatic alignment switch 61 (referring to the flowchart in FIG. 13). When the patient's eye enters into the range that the pupil edge of the lateral-longitudinal directions may be detected by the eye position detecting system, the computer 9 calculates the center position of the pupil by processing the signal from CCD camera 29 as described above, so that the arm part 2 may be moved in X-Y directions by drive-and-controlling the driving devices 31 and 32 under the control of the controlling device 40 so as to be congruent the optical axis of the laser beam irradiation with the center position of the pupil.

In the case of performing the laser beam irradiation with keeping that the optical axis of the laser beam irradiation is congruent with the center position of the pupil, firstly, the completion of alignment is confirmed, then the Ready switch 62 on the controller 6 is pressed. The predetermined position on the photographic element of CCD camera 29 (the position of the optical axis of the laser beam irradiating optical system) is stored as a standard position so that the standard position may be congruent with the center position of the pupil (within the predetermined permissible range). Then, an eye tracking mechanism for moving the arm part 2 is made to go into run under the control of the controlling device 40. The center position of the pupil which is obtained by processing a signal from CCD camera 29 is compared with the standard position at any time. When the patient's eye E is moved beyond the predetermined permissible range, the X-direction and Y-direction arm driving devices 31 and 32 are driven by the controlling device 40 based on the comparison information which is transmitted by the computer 9 so as to move the arm part 2 in X-Y directions and to lead the center position of the pupil within the predetermined permissible range of the standard position. Also, when the eye tracking mechanism is operated by inputting the signal of the Ready switch 62, it is confirmed that the eye E may be possible to track. Then, a safe-shutter device 41 is opened so that it may become such condition that the laser beam irradiation by the foot switch 8 can be performed.

When the operator steps on the foot switch 8, the laser beam is emitted by the controlling device 40. The excimer laser beam is irradiated on the patient's eye E through the laser beam irradiating optical system, and the desired area of the cornea Ec is ablated only for the set level. Referring to the eye position detecting system of the present apparatus, the level of the quantity of light from the pupil part is higher than that of the periphery because of illumination from the rear side by the reflected light of the fundus of the eye E. Therefore, it can be performed easily to detect the pupil edge and the pupil center without being effected deformation of the corneal shape caused by the ablation. Therefore, the ablation can be performed under the condition that the eye is tracked accurately. In the case that the patient's eye E is moved beyond the moving range of X-Y directions of the arm part 2 upon the laser beam irradiation, the safe-shutter device 41 is operated so as to block off the laser beam irradiation.

In the case that the laser beam irradiation is performed under the condition that the optical axis of the laser beam irradiation is aligned at will with the cornea of the eye E, the alignment is performed so as to be a target position by handling the joystick 7.

The alignment is completed, and once the Ready switch 62 is pressed, then the coordinate position of the pupil center on the photographic element of CCD camera 29 is stored as a standard position by the computer 9 (upon operating the automatic alignment, when operation signal of the joystick 7 is inputted, the coordinate position of the pupil center, which is obtained by offsetting its share, is stored as standard position). In the case that the eye E is moved, the eye tracking mechanism for moving the arm part 2 is operated under the control of the controlling device 40 so that the detected pupil center may be congruent with the stored standard position (may enter the predetermined permissible range). When the signal from the foot switch 8 is inputted, the excimer laser beam is irradiated as the same way mentioned above, therefore the desired range of the cornea Ec is ablated only for the set level.

The ablation is completed, then the V. facter observing changing-over switch 63 of the controller 6 is turned on. The controlling device 40, which received the signal from the V. facter observing changing-over switch 63, makes the safe-shutter or the like go into run in order to stop the laser beam irradiation, also makes the photographic lens 27 be driven so that the photographing surface of CCD camera 29 may be approximately conjugate with the position close to the cornea optically. The infrared light emitted from the infrared illumination light source 24 is incidence on CCD camera 29 by traveling along the above-mentioned course. The retro-illumination image of the anterior part of the eye E which is photographed by CCD camera 29 is transmitted to the computer 9 so as to be displayed on the monitor 74. The operator observes the retro-illumination image of the cornea which is displayed on the monitor 74 so as to estimate whether another operation is necessary or not, and then, the operator determines another operation or the finish of the operation.

However, in the case that the operator cannot judge only by the shadow of the retro-illumination image of the cornea, the judgement may be determined by the above-mentioned color map which is drawn by the image analyzing-processing means.

In the above-mentioned preferred embodiment, although the retro-illumination image of the cornea is displayed on the monitor of the computer, it is possible to equip with a separated monitor. As concerns the monitor, not only a cathode-ray tube of the preferred embodiment but also any various monitor such as a small-size monitor like liquid crystal display (LCD) may be also available. Further, although the controller is equipped with the V. facter observing changing-over switch, it may be possible to be changed overs by using the keyboard operation of the computer.

In the preferred embodiment, although the detection of the eye is processed by the computer 9, it is also possible to process by using the controlling device 40.

The present invention is not restricted only by the preferred embodiment, also various modifications may be possible. The present invention may achieve without any relation of structure of optical system of the laser beam irradiating optical system for the correction of ametropia or the like.

The foregoing description of the preferred embodiment of the invention has been presented for purposes of illustration and description. It is not intended to be exhaustive or to limit the invention to the precise form disclosed and modifications and variations are possible in light of the above teachings or may be acquired from practice of the invention. The embodiment chosen and described in order to explain the principles of the invention and its practical application to enable one skilled in the art to utilize the invention in various embodiments and with various modifications as are suited to the particular use contemplated.

It is intended that the scope of the invention be defined by the claims appended hereto, and their equivalents.

What is claimed is:

1. A corneal surgical apparatus for ablating an area of a cornea in a patient's eye comprising:

an observation optical system for observing an anterior part of the patient's eye;

a laser beam irradiating optical system for irradiating a laser beam which causes the corneal ablation; and an eye tracking unit that performs tracking between an irradiation position of the laser beam of said laser beam irradiating optical system and the patient's eye, said eye tracking unit comprising:

an illumination optical system that projects an illumination light into the patient's eye throught a pupil and illuminates the anterior part by the illumination light reflected at a fundus;

a photographic element for photographing a retro-illumination image of the pupil illuminated by the reflected illumination light and for providing a signal;

image processing means for processing the signal of the retro-illumination image of the pupil transmitted from said photographic element and locating an edge of the pupil;

determining means for determining a moving direction and an amount of movement based on a position of the edge of the pupil located by said image processing means;

a control unit that controls movement of said laser beam irradiating optical system relative to the patient's eye based on data determined by said determining means.

2. The corneal surgical apparatus according to claim 1, further comprising:

focus position moving means for moving a focus position of the reflected light so as to selectively photograph the retro-illumination image of the pupil or a retro-illumination image of the cornea by said photographic element; and displaying means for displaying the retro-illumination image of the cornea photographed by said photographic element in order to estimate whether corneal surgery has been properly performed.

3. The corneal surgical apparatus according to claim 2, wherein said display means displays the image of the cornea in a manner of a color map.

4. The corneal surgical apparatus according to claim 1, further comprising:

irradiation-signal generating means for generating a signal for completing the tracking and permitting laser beam irradiation at the time when said irradiating position and the patient's eye have a predetermined positional relationship.

5. The corneal surgical apparatus according to claim 1, wherein said image processing means locates the edge of the pupil based on a distribution of light volume of the retro-illumination image of the pupil.

6. The corneal surgical apparatus according to claim 5, wherein said image processing means obtains a position of a pupil center by obtaining the center of the edge of the pupil, and said determining means determines the moving direction and the amount of movement based on the position of the pupil center.

7. The corneal surgical apparatus according to claim 5, wherein said image processing means locates the edge of the pupil by differentiating the distribution of the light volume of the retro-illumination image of the pupil.

8. The corneal surgical apparatus according to claim 1, wherein an optical axis of said observation optical system is coincided with an optical axis of said laser beam irradiating optical system, whereby said observation optical system is also moved by said eye tracking unit.

9. A corneal surgical apparatus for ablating an are a of a cornea in a patient's eye, comprising:

a laser beam irradiating optical system for irradiating a laser beam which causes the corneal ablation;

moving means for moving an irradiation position of the laser beam by said laser beam irradiating optical system relatively with respect to the patient's eye;

an observation optical system for observing an anterior part of the patient's eye;

an illumination optical system that projects an illumination light into the patient's eye through a pupil and illuminates the anterior part by the illumination light reflected at a fundus;

a photographic element for photographing a retro-illumination image of the pupil illuminated by the reflected illumination light and providing a signal;

image processing means for processing the signal of the retro-illumination image of the pupil transmitted from said photographic element and obtaining an edge of the pupil;

determining means for determining a moving direction and an amount of movement based on a position of the edge of the pupil obtained by said image processing means; and controlling means for driving and controlling said moving means based on the moving direction and the amount of movement determined by said determining means.

10. The corneal surgical apparatus according to claim 9, further comprising:

focus position moving means for moving a focus position of the reflected light so as to photograph the retro-illumination image of the pupil or the retro-illumination image of the cornea by said photographic element selectively; and a monitor for displaying the retro-illumination image of the cornea photographed by said photographic element in order to estimate whether corneal surgery has been properly performed.

11. The corneal surgical apparatus according to claim 10, wherein said monitor displays the image of the cornea in a manner of a color map.

12. The corneal surgical apparatus according to claim 9, wherein said image processing means locates the edge of the pupil based on a distribution of light volume of the retro-illumination image of the pupil.

13. The corneal surgical apparatus according to claim 12, wherein said image processing means obtains a position of a pupil center by obtaining the center of the edge of the pupil, and said determining means determines the moving direction and the amount of movement based on the position of the pupil center.

14. The corneal surgical apparatus according to claim 12, wherein said image processing means obtains the edge of the pupil by differentiating the distribution of the light volume of the retro-illumination image of the pupil.

15. The corneal surgical apparatus according to claim 9, wherein an optical axis of said observation optical system is coincided with an optical axis of said laser beam irradiating optical system, whereby said observation optical system is also moved by said moving means.

16. The corneal surgical apparatus according to claim 9, further comprising:

irradiation-signal generating means for generating a signal for completing alignment and permitting laser beam irradiation when said irradiating position and the patient's eye have a predetermined positional relationship realized by said moving means.

17. A corneal surgical apparatus for ablating an area of a cornea in a patient's eye, comprising:

an observation optical system for observing an anterior part of the patient's eye, a laser beam irradiation optical system for irradiating a laser beam which causes the corneal ablation;

an illumination optical system that projects an illumination light into the patient's eye through a pupil and illuminates the anterior part by the illumination light reflected at a fundus;

a photographic element for photographing a retro-illumination image of the cornea illuminated by the reflected illumination light;

display means for displaying the retro-illumination image of the cornea photographed by said photographic element in order to estimate whether corneal surgery has been properly performed.

18. The corneal surgical apparatus according to claim 17, wherein said display means displays the image of the cornea in a manner of a color map.

* * * * *

UNITED STATES PATENT AND TRADEMARK OFFICE
CERTIFICATE OF CORRECTION

PATENT NO.: 6,030,376

DATED: February 29, 2000

INVENTOR(S): Arashima et al.

It is certified that an error appears in the above-identified patent and that said Letters Patent is hereby corrected as shown below:

Inventors, Front Page, line 2, change "Hanai" to --Hanaki--.

Abstract, Front Page, line 9, change "being" to --is--.

Claim 6, col, 11, line 9, change "obtains" to --locating--; and
        line 10, change "obtaining" to --locating--.

Claim 9, col. 11, line 25, change "are a" to --area--;
        line 44, change "obtaining" to --locating--; and
        line 48, change "obtained" to --located--.

Claim 13, col. 12, line 15, change "obtains" to --locates--; and
        line 16, change "obtaining" to --locating--.

Claim 14, col. 12, line 21, change "obtains" to --locates--.

Claim 17, col. 12, line 39, change "," to --;--.

Signed and Sealed this

Third Day of April, 2001

Attest:

NICHOLAS P. GODICI

Attesting Officer    Acting Director of the United States Patent and Trademark Office